United States Patent [19]

Bier

[11] Patent Number: 5,162,650
[45] Date of Patent: Nov. 10, 1992

[54] METHOD AND APPARATUS FOR MULTI-STAGE PARTICLE SEPARATION WITH GAS ADDITION FOR A MASS SPECTROMETER

[75] Inventor: Mark E. Bier, San Mateo County, Calif.

[73] Assignee: Finnigan Corporation, San Jose, Calif.

[21] Appl. No.: 645,649

[22] Filed: Jan. 25, 1991

[51] Int. Cl.$^5$ .............................................. H01J 49/26
[52] U.S. Cl. ................... 250/288; 250/281; 250/282
[58] Field of Search ............ 250/288, 288 A, 281, 250/282; 55/17, 270; 73/863.21, 863.22

[56] References Cited

U.S. PATENT DOCUMENTS

| | | | |
|---|---|---|---|
| 4,531,056 | 7/1985 | Labowsky et al. | 250/288 A |
| 4,686,367 | 8/1987 | Louris et al. | 250/291 |
| 4,749,860 | 6/1988 | Kelley et al. | 250/291 |
| 4,885,076 | 12/1989 | Smith et al. | 250/288 |
| 4,948,962 | 8/1990 | Mitsui et al. | 250/288 |
| 4,960,992 | 10/1990 | Vestal et al. | 250/288 |
| 5,015,845 | 5/1991 | Allen et al. | 250/288 |

Primary Examiner—Jack I. Berman
Assistant Examiner—Kiet T. Nguyen
Attorney, Agent, or Firm—Flehr, Hohbach, Test, Albritton & Herbert

[57] ABSTRACT

Disclosed is a multi-stage particle separator for separating analyte from non-analyte solvent in a fluid sample having nebulizing means to form droplets from the liquid sample and means coupled to the nebulizing means for adding helium to the nebulizing means. Furthermore, the multi-stage particle separator has a desolvation chamber for receiving the droplets, the desolvation chamber terminating in a nozzle, a multi-stage momentum separator including skimmers, and means for introducing a gas into one or more of the states to increase pressure of the latter stage so that the particles leave the multi-stage separator substantially free of solvent.

6 Claims, 7 Drawing Sheets

METHOD AND APPARATUS FOR MULTI-STAGE PARTICLE SEPARATION WITH GAS ADDITION FOR A MASS SPECTROMETER

BRIEF DESCRIPTION OF THE INVENTION

This invention relates generally to a multi-stage particle separator and method in which enhanced separation of the analyte from non-analyte occurs before introduction to a mass spectrometer.

BACKGROUND OF THE INVENTION

The identification of analytes eluting from a liquid chromatography column is expedited with the combined use of a particle beam (PB) interface and a mass spectrometer [1,2]. The technique is unique in that although analytes enter the PB interface while in solution, the data usually obtained are electron impact (EI) mass spectra. The EI spectra acquired are library searchable, which further aids in the identification of the molecule. The compounds may also be chemically ionized (CI) [2] for molecular weight determination or for improved signal response in mass spectrometry/mass spectrometry experiments. In addition to these advantages, PB offers an inlet for compounds that are thermally unstable and/or are not volatile enough for efficient GC/MS analysis without chemical modification. The ability to obtain an EI mass spectrum combined with these other benefits has lead many mass spectrometer manufacturers to develop particle beam interfaces for use on quadrupole instruments [3].

Prior to the PB interface, only membrane [4,5,6] and moving belt interfaces [7,8,9,10,11] have allowed for the generation of both EI and CI spectra from an analyte initially in a liquid solution. Dimeethyl-vinyl silicon polymer membrane interfaces have shown high sensitivity, but primarily for volatile nonpolar molecules and thus, one of their main uses has been in the analysis of volatile organics in water and in reaction monitoring [12]. The moving belt apparatus has been successful when looking at analytes in high concentrations of water [13] and has been used to detect molecules in the picogram range [9], but it can have memory effects and is considered cumbersome by many. Other techniques such as thermospray [14], electrospray [15], and flow fast atom bombardment (FAB) [16,17] are used as on-line continuous liquid chromatography interfaces, but they produce "CI-like" mass spectra and also give little structural information. Recently particle beam interfaces have been used to introduce analyte into the matrix during fast atom bombardment ionization (FAB) [18,19]. The sensitivity was low, as expected due to analyte loss in the interface, but the experiment demonstrates a novel method of sample addition.

Although improvements have been made to the particle beam interface [20], the concept of using stages of momentum separation to enrich the beam with particles and to remove solvent molecules has remained unchanged. In PB systems, a liquid solution is nebulized into micrometer-sized droplets which are partially desolvated and accelerated through a nozzle. Once through the nozzle, high velocity particles are momentum separated from solvent molecules by a skimmer and are then transferred to the next stage of momentum separation. The enrichment region has traditionally consisted of two stages of momentum separation followed by a transfer line [1,2,3]. Once separated from the solvent, the particles are transmitted to the ion source of a differentially pumped mass spectrometer for vaporization and ionization. The particle separation does have its limitations, such as changes in the analyte response, due to a coelution carrier process [21] and a non-linear calibration curve which reduces the simplicity of quantitative analysis [2], but the technique is unique in its ability to produce EI spectra.

In liquid chromatography/mass spectrometry (LC/MS), it is crucial to reduce the partial pressure of the solvent or unwanted molecules that reach the mass spectrometer. This becomes even more important in non-differentially pumped quadrupole and ion trap mass spectrometers.

This invention describes a novel three-stage particle beam interface with a gas addition port. The particle separator can be used to couple an LC to an ion trap mass spectrometer. The interface uses an additional stage of momentum separation before transmitting the particles to the ion trap and incorporates the addition of make-up gas to improve jet separation and maintain optimum ion trap helium pressure. Particles pass directly into the trapping chamber, where they are vaporized and ionized to produce EI mass spectra.

OBJECTS AND SUMMARY OF THE INVENTION

It is an object of this invention to provide a mass spectrometer with a particle separation device for detecting analyte in liquid solutions.

It is a further object of the invention to provide a quadrupole ion trap mass spectrometer with a particle separation device for detecting analyte in liquid solutions.

It is a further object of the invention to provide a nondifferentially pumped quadrupole mass spectrometer with a particle separation device for detecting analyte in liquid solution.

It is a further object of the invention to provide a mass spectrometer with enhanced signal-to-noise when using a particle separator of the type described.

This invention describes a novel, three-stage particle beam interface with a gas addition port. The particle separator can be used to couple an LC to an ion trap mass spectrometer. The interface uses an additional stage of momentum separation before transmitting the particles to the ion trap and incorporates the addition of make-up gas to improve jet separation and maintain optimum ion trap helium pressure. Particles pass directly into the trapping chamber, where they are vaporized and ionized to produce EI mass spectra.

BRIEF DESCRIPTION OF THE DRAWINGS

The foregoing and other objects of this invention will be more clearly understood from the following description when read in conjunction with the accompanying drawings, in which.

DESCRIPTION OF PREFERRED EMBODIMENT

Figures 1, 1A:
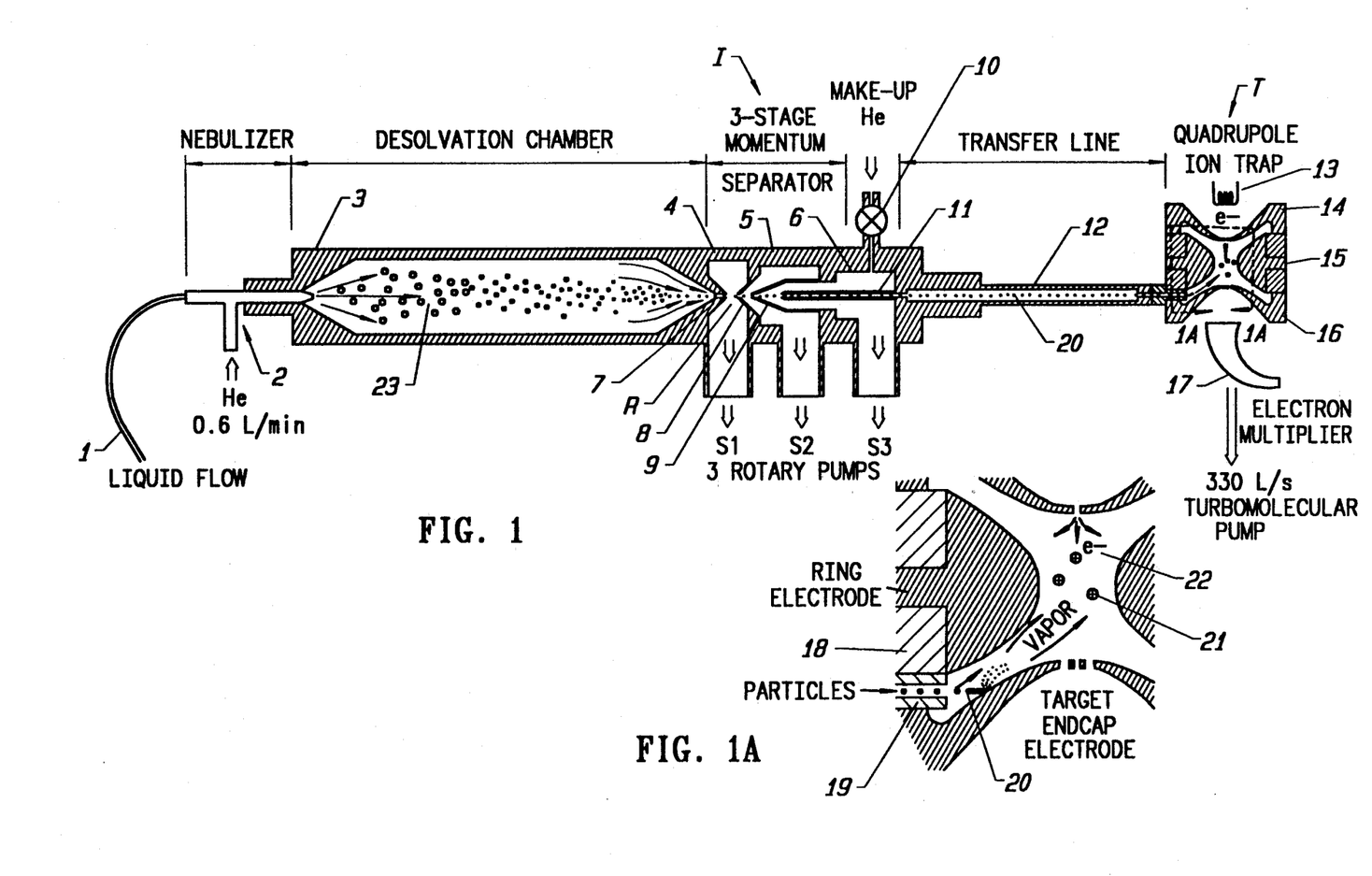
FIG. 1 is a schematic view of the three-stage particle beam interface showing the addition of helium to stage three.
Figure 2:
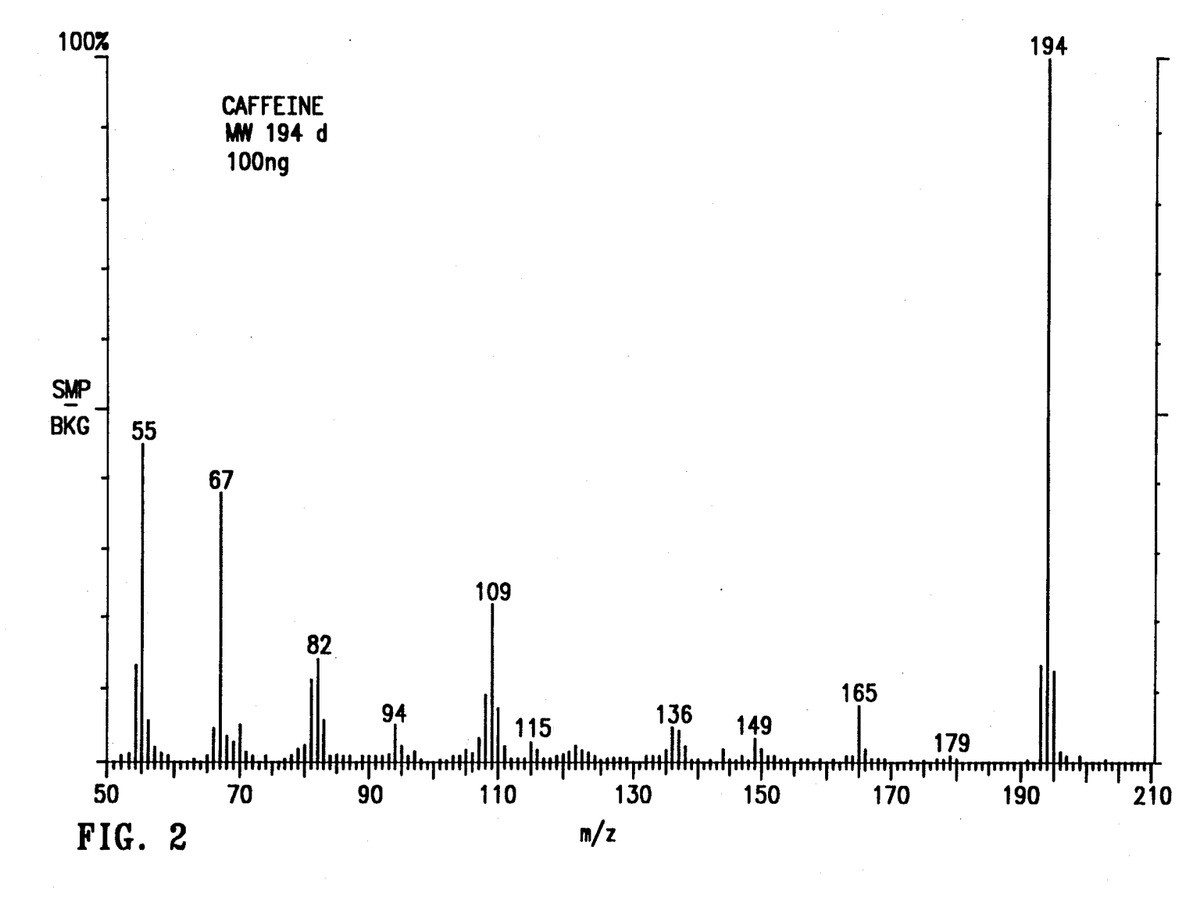
FIG. 2 is an electron impact mass spectrum of 100 ng caffeine using the particle separator device.
Figure 3:
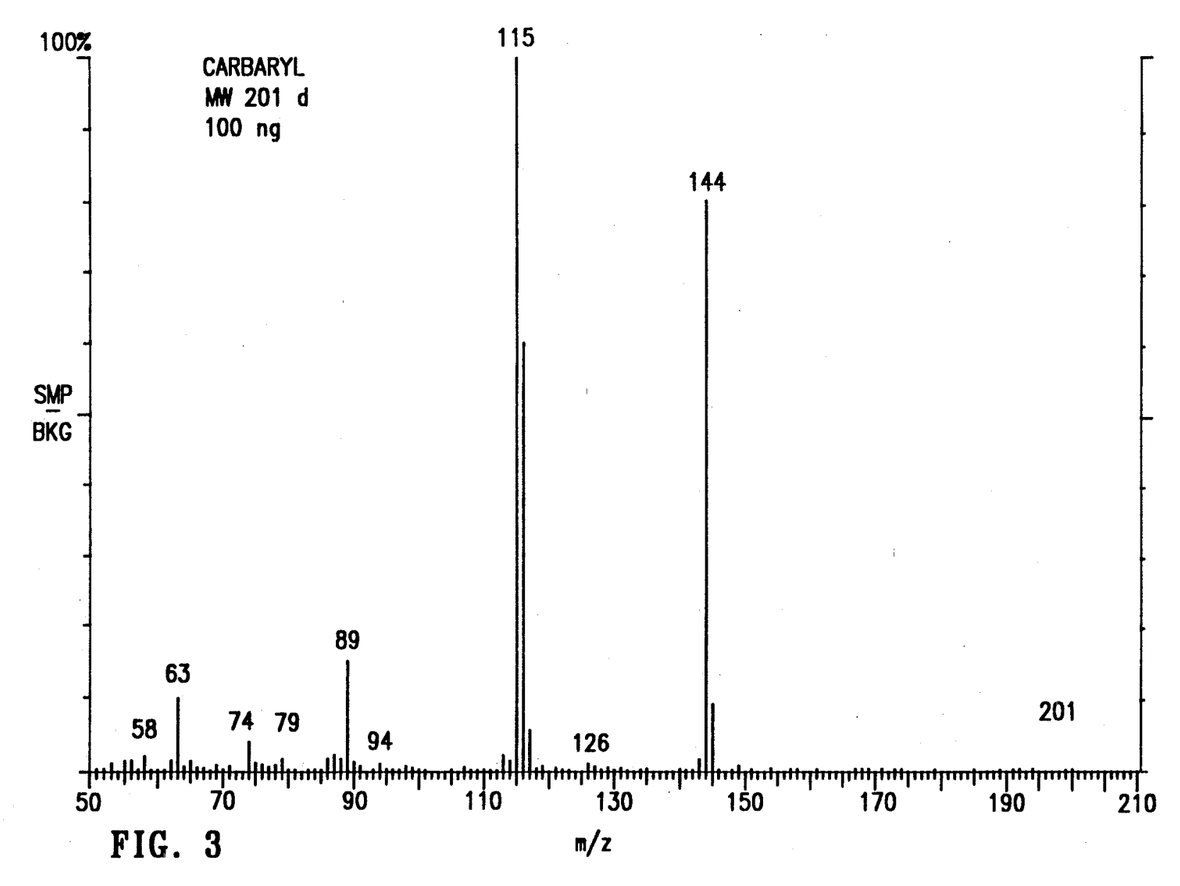
FIG. 3 is an electron impact spectrum of 100 ng carbaryl using the particle separator device.
Figure 4:
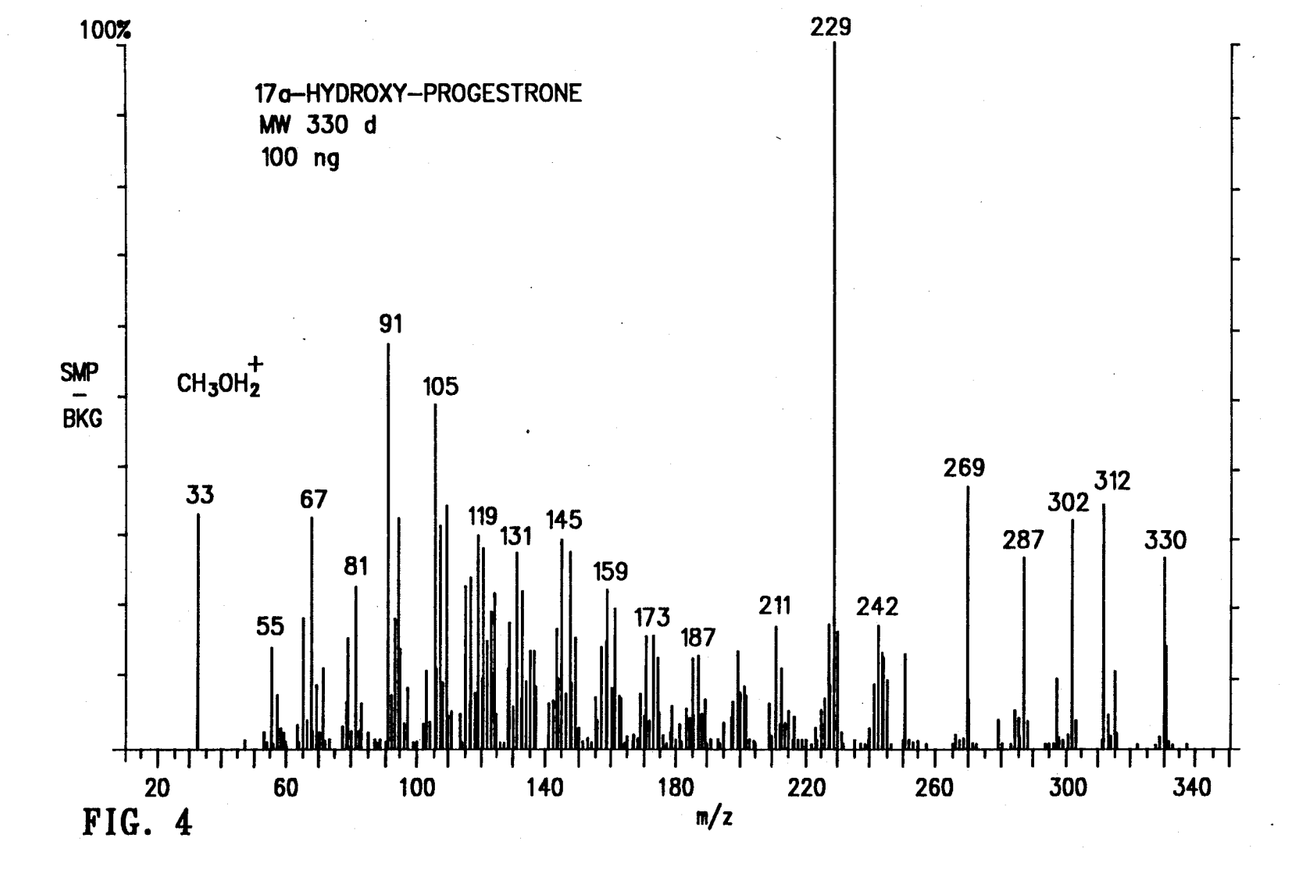
FIG. 4 is an electron impact spectrum of 100 ng 17α-hydroxyprogesterone, M=330, using the particle separator device.
Figure 5:
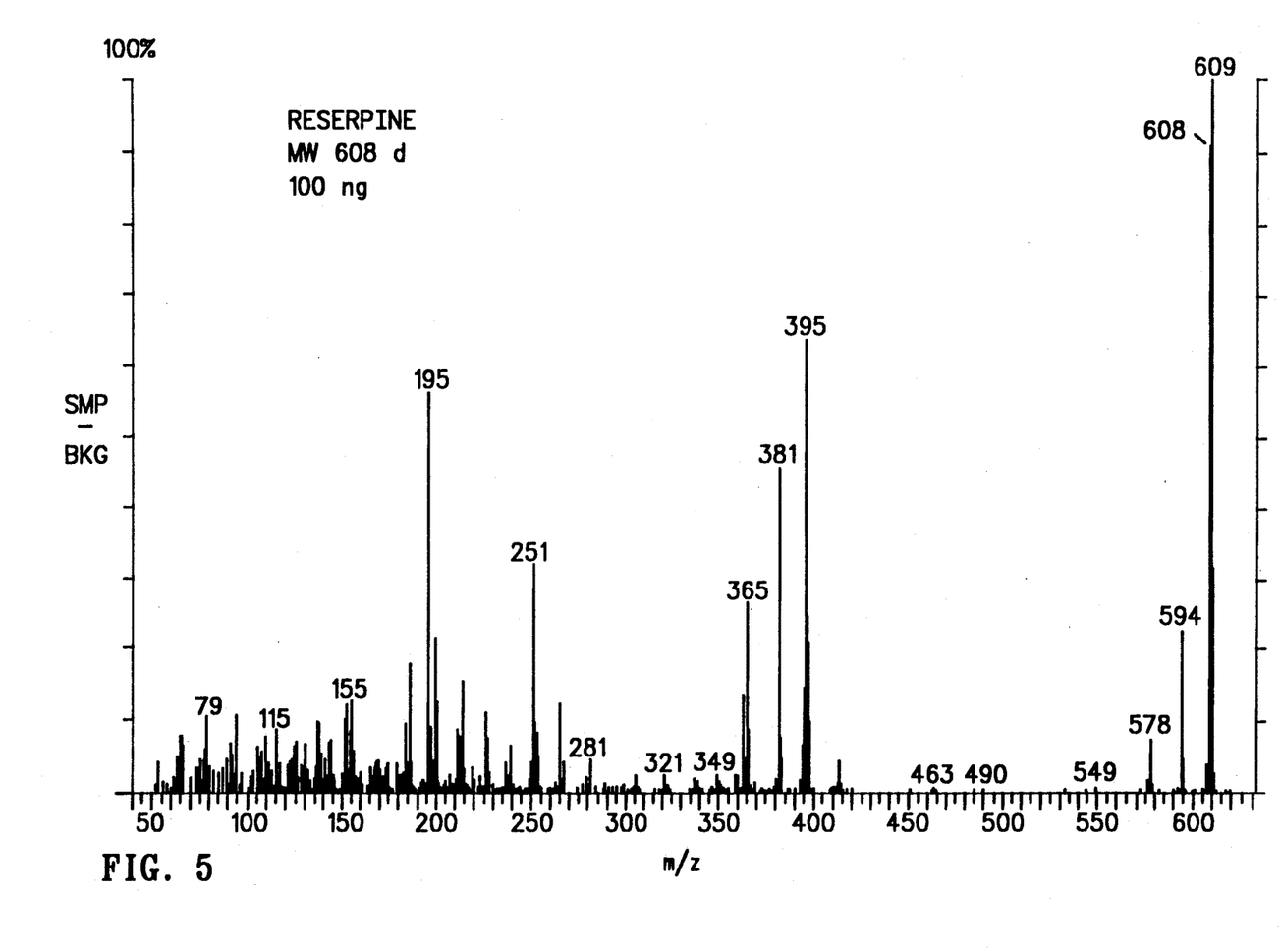
FIG. 5 is an electron impact spectrum of 100 ng reserpine, M=608, using the particle separator device.

A quadrupole ion trap mass spectrometer system embodying the present invention is schematically illustrated in FIG. 1. The PB interface ion trap system receives liquid from a liquid chromatograph pump on level, an injection system 2 introduces the liquid into a three-stage particle beam interface I, and a quadrupole ion trap mass spectrometer T.

The particle beam interface in accordance with the invention incorporates a pneumatic nebulizer, a heated aluminum desolvation chamber, a nozzle 7, a three-stage momentum separator, and a stainless steel transfer line as shown in FIG. 1.

The liquid solution is pumped through the high pressure LC stainless steel tubing, a 15 cm length of fused silica capillary tubing 1, and into a Meinhard pneumatic nebulizer 2. The nebulizer shears the liquid eluting at the tip into droplets with a concentric flow of helium. The high surface area droplets 23 are directed at relatively low velocity toward the entrance of the nozzle 7 and are desolvated as they flow through the heated desolvation chamber 3. Heaters (not shown) are used to supply the heat of vaporization for the solvent and to maintain the desolvation chamber temperature at its set point. The droplets 23 are expected to be desolvated to the point where only slightly solvated analyte droplets remain.

The remaining droplets and newly formed particles are directed by the flow of helium and solvent through the nozzle 7. The nozzle has a small orifice in the range of 0.5 mm and an aspect ratio in the order of 10:1. The particles in the nozzle increase in velocity by one to two orders of magnitude and exit the nozzle at a supersonic flow rate. The gas, exits into a region R at a pressure of several Torr, stage one, where a shock wave is created. The shock wave is configured into a barrel shock wave encompassing the axis of the beam and a mach disk which is located at the end of the barrel shock. The mach disk is perpendicular to the particle beam. The shock wave is the result of the gas molecules traveling faster than the speed of sound in that medium [22].

The position of the mach disk between the nozzle and skimmer one (8) is important to obtain optimum performance of the momentum separation interface. But the trajectories of large particles 20 at high velocities (high momentum) are not greatly perturbed by the gas flow lines and tend to maintain a straight path. This allows particles to be separated from the rest of the beam by the skimmers. The particle separation that occurs in stage two (5) involves a mach disk located 1.3 mm from the back side of skimmer one (8), but the gas making up this disk is less dense than the mach disk found in stage one (4). The pressure typically measured in the second stage was 200 mT. Stage three (6) includes a facility for the addition of helium 10 and the pressure here is approximately equal to that in stage two. The third stage receives some solvent by diffusion through skimmer two (9), but the amount of solvent found in stage three is minimal compared with the other stages. Maintaining stage three at 200 mTorr also insure that no oil may backstream from the pumps to the interface due to the flow into the rotary pumps. The diameters of the skimmers one (8), two (9) and three (11) may be, for example, 0.5 mm, 0.5 mm, and 2.5 mm, respectively, along the axis of flow. The spacings used for the examples to follow were 5 mm between the nozzle and skimmer one, 5 mm between skimmer one and skimmer two, and 16 mm between skimmer two and skimmer three. Three rotary vane vacuum pumps were used to remove the solvent from the interface.

Once leaving the momentum separator region, the analyte particles 20 are transferred to the ion trap through a stainless steel transfer line 12. The transfer line is sealed to the ion trap body with a tip 19 which is fitted into the ion trap opening normally used for a GC transfer line. The particles 20 remaining on axis are thereby directed to the endcap of the quadrupole ion trap. The particles strike the hot stainless steel hyperbolic surface of the endcap 16 where they are vaporized. Once vaporized, the molecules are ionized and the ions 21 are trapped in the center of the quadrupole trapping field of the ion trap.

In one example, helium was added to stage three of the particle separator at an elevated pressure. For example, pressure of 200 mTorr in stage three limited the amount of solvent that would otherwise reach stage three and it also created a viscous flow condition from stage three to the rotary vane pump and thus stopped pump oil from backstreaming.

Other gases besides helium may be suitable for use in the particle separator such as nitrogen, argon, neon or others. The gas may also find the same use in other stages besides stages three. For example one might add gas to a particle separator in stage two or some latter stage of a multi-stage particle separator.

The ion trap T used was a modified Finnigan ITS40. The additional helium added to the ion trap through stage three of the particle beam interface was necessary in maintaining an operating pressure at approximately $1 \times 10^{-3}$ Torr in the trapping chamber. One millitorr of helium presumably damps the ion trajectories to the center of the trap greatly enhancing the resolution and sensitivity of high mass ions [23]. The ion trap manifold was heated to a temperature of 220° C. by a heater jacket which transfers heat to the target endcap radiantly and through conduction of the stainless steel mounting posts and ceramic spacers. A warm-up period of four hours was used to allow the endcap to reach an equilibrium temperature of 170°-175° C. The endcap serves a dual purpose in this instrument—a heated target for vaporizing the particles and an electrode used to form one pole of the quadrupole field. The ions trapped by the quadrupole field were ejected using mass selective instability scanning [24] and detected using an electron multiplier.

To avoid space charging caused by forming too many ions and to limit any interaction between the solvent molecules and/or ions with the analyte, it is desirable to have the lowest possible number of solvent ions in the trap. This becomes even more important for an ion trap than for a quadrupole instrument because the long resident times found in ion trap mass spectrometers can lead to ion/ion interactions. A three- rather than two-stage particle beam interface with gas addition reduces the number of solvent molecules in the trap.

Table 1 shows typical operating conditions for a particle beam quadrupole ion trap system in accordance with the invention.

TABLE 1

Typical Operating Parameters for the Particle Separator used on a Quadrupole Ion Trap Mass Spectrometer.

| | |
|---|---|
| Liquid flow rate | 0.5 ml/min |
| Injection loop volume | 20 μl |
| Nebulizer flow rate, He | 0.6 l/min |
| Desolvation temperature | 50° C. |
| Ion trap temperature | 172° C. |
| Manifold temperature | 220° C. |
| Desolvation pressure | 250 Torr |
| Stage 1 pressure | 3 Torr |
| Stage 2 pressure | 200 mTorr |
| Stage 3 pressure | 200 mTorr He |
| Ion trap pressure | $1 \times 10^{-3}$ Torr He |
| Analyzer pump speed | 330 l/s |
| Multiplier gain | $10^5$ |

Figure 6:
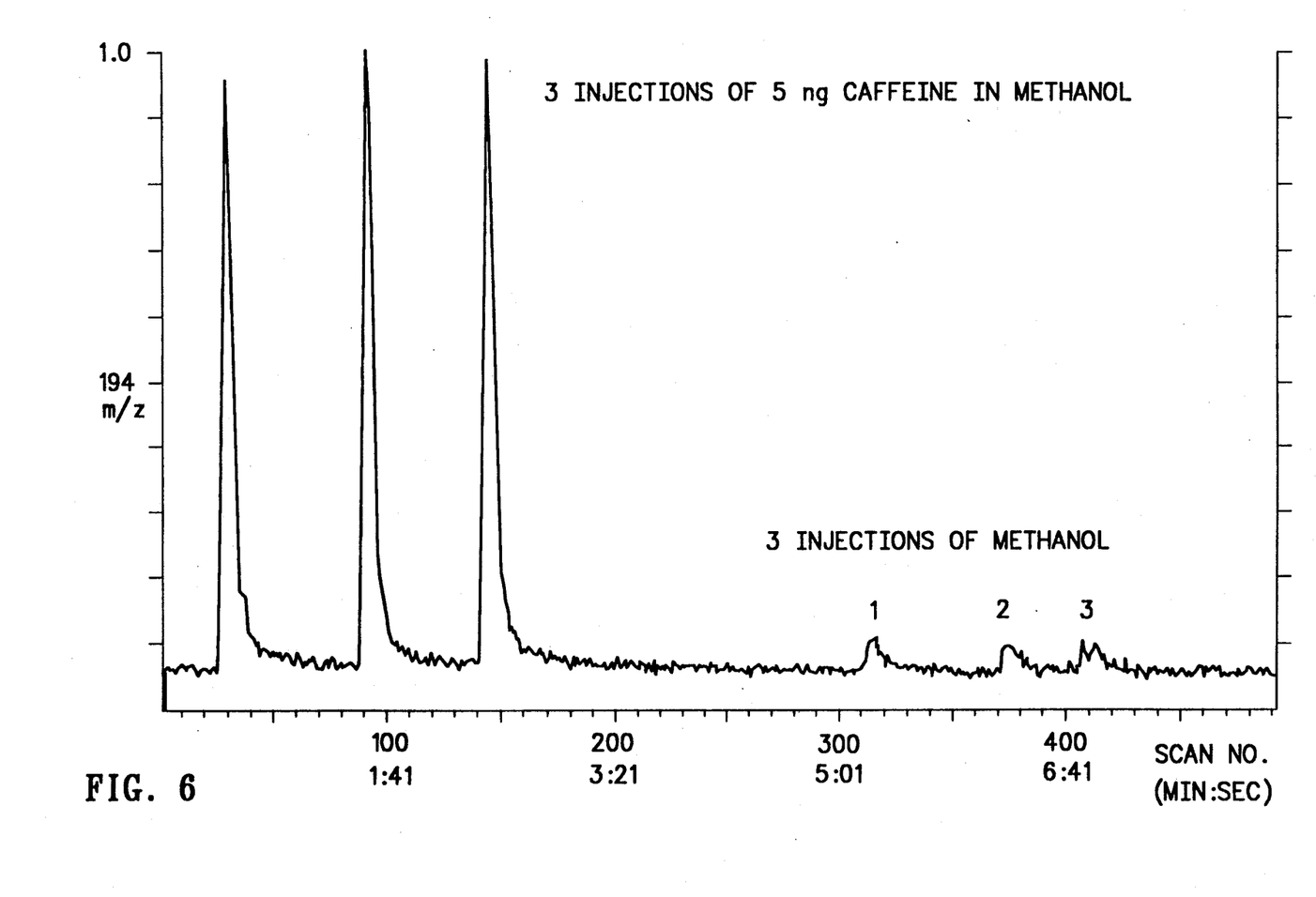
FIG. 6 is a graph of three peaks of M=194 showing the detection limit of 5 ng for caffeine followed by three injections of pure methanol.
Figure 7:
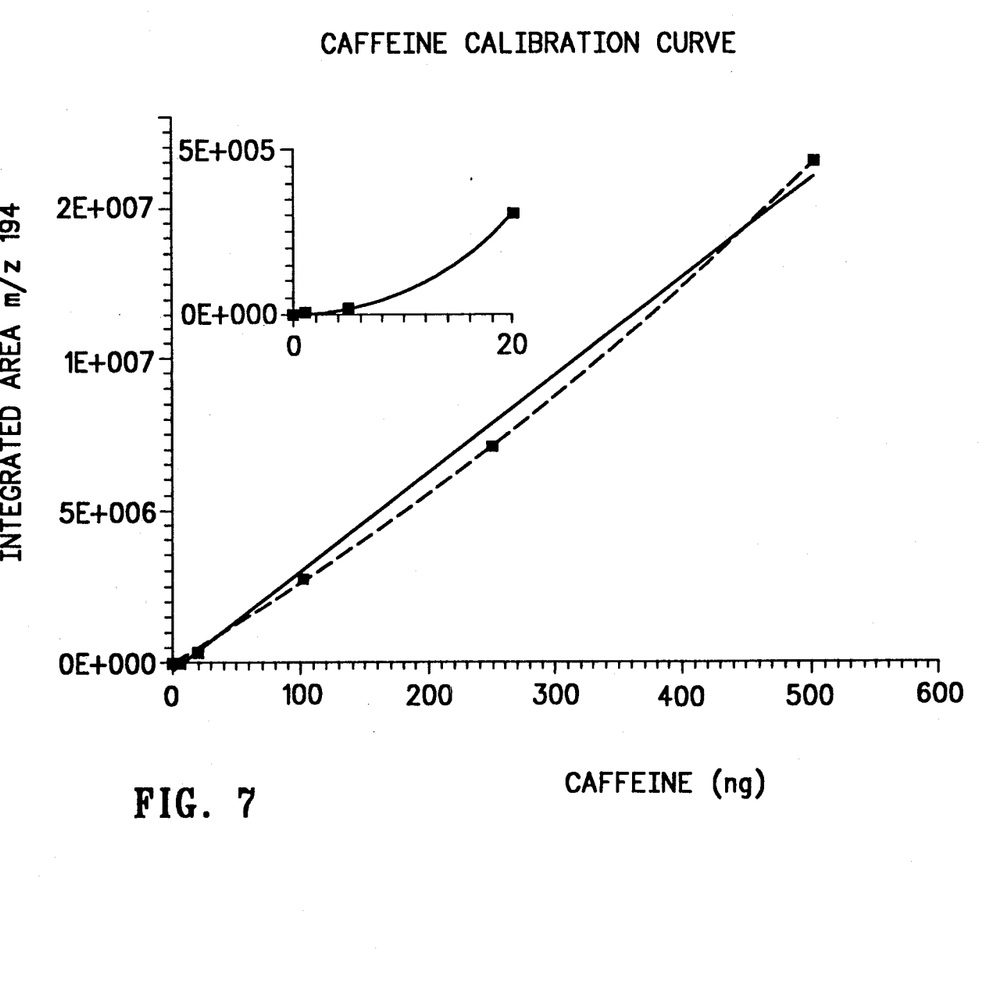
FIG. 7 is a calibration curve of caffeine from 1 ng to 500 ng. Nonlinearity is shown at lower analyte concentrations and is attributed to poor enrichment of smaller particles in the beam. The dashed curve is a power two, polynomial fit.

To test the coupling of the three stage particle beam interface to a quadrupole mass spectrometer, initial experiments used methanol Four compounds were used to assess the quality of the EI spectra produced. The electron impact (EI) spectra of caffeine (molecular ion 194), carbaryl (molecular ion 201), 17α-hydroxy-progesterone (molecular ion 330) and reserpine (molecular ion 608) were collected from injections of the individual compounds at 100 ng. This data is observed in FIGS. 2 through 5, respectively. FIG. 6 shows the signal response for three injections on 5 ng caffeine. A calibration curve was obtained for samples of between 1 and 500 ng caffeine to ascertain the linearity of the system response and is shown in FIG. 7.

The device may also be used on a quadrupole or other mass analyzer in which additional separation of background molecules would enhance the signal to noise ratio. A non-differentially pumping quadrupole mass spectrometer would be one type of instrument that may benefit from this type of particle separator device.

1. Willoughby, R. C.; Browner, R. F. Anal. Chem., 1984, 56, 2626.
2. Winkler, P. C. Ph.D. Thesis, Georgia Institute of Technology, 1986.
3. Extrel (Pittsburgh, Pa.), Finnigan MAT (San Jose, Calif.), Hewlett-Packard (Palo Alto, Calif.), VG Instruments (Cheshire, England) and Vestec (Houston, Tex.).
4. Llewellyn P. M.; Littlejohn D. P. U.S Pat. No. 3,429,105, February 1969.
5. Jones, P. R.; Yang, S. K. Anal. Chem. 1975, 47, 1000.
6. Bier, M. E.; Cooks, R. G. Anal. Chem. 1987, 59, 597.
7. Scott, R. P. W.; Scott, C. G.; Munroe, M.; Hess, J. J. Chromatogr. 1974, 99, 395.
8. McFadden, W. H.; Schwartz, H. L.; Evans, S. J. Chromatogr. 1976, 122, 389.
9. Van Der Greef, J.; Tas, A. C.; Ten Noever De Brauw, M. C.; Höhn, M.; Meuerhoff, G.; Rapp, U. J. Chromatogr. 1985, 323, 81.
10. Levsen, K.: Schäfer K. H.; Dobberstein, P. Biomed. Mass Spectrom. 1984, 11, 308.
11. Games, D. E.; McDowall, M. A.; Levsen, K.; Schafer, K. H.; Dobberstein, P; Gower, J. L. Biomed. Mass Spectrom. 1984, 11, 87.
12. Bier, M. E.; Kotiaho, T.; Cooks R. G. Analytica Chimica Acta, 1990, 231, 175.
13. Kresbach, G. M.; Baker, T. R.; Nelson, R. J.; Wronka, J.; Karger, B. L.; Vouros, P. J. Chromatogr. 1987, 394, 89.
14. Blakely, C.; Vestal, M. Anal. Chem. 1983, 55, 750.
15. Whitehouse, C.; Dreyer, R.; Yamashita, M.; Fenn, J. Anal. Chem. 1985, 57, 675.
16. Ito, Y.; Takeuchi, T.; Ishi, D.; Goto, M. J. Chromatogr. 1985, 346, 161.
17. Caprioli, R.; Fan, T.; Cottrell, J. Anal. Chem. 1986, 58, 2949.
18. Sanders, P. E.; Willoughby, R. C.; Mitrovich, S. Presented at the 37th ASMS Conference on Mass Spectrometry and Allied Topics, Miami Beach, Fla., 21–26 May 1989, 110.
19. Kirk, J. D.; Browner, R. F. Presented at the 37th ASMS Conference on Mass Spectrometry and Allied Topics, Miami Beach, Fla, 21–26 May 1989, 131.
20. Winkler, P. C.; Perkins, D. D.; Williams, W. K.; Browner, R. F. Anal. Chem. 1988, 60, 489.
21. Bellar, T. A.; Beymer, T. D.; Budde, W. L. J. American Soc. Mass Spectrom. 1990, 1, 92.
22. John, J. E. A. In Gas Dynamics, Allyn and Bacon: Boston, 1969.
23. Louris, J. N.; Cooks, R. G.; Syka, J. E. P.; Kelley, P. E.; Stafford, G.; Todd, J. F. J. Anal. Chem. 1987, 57, 1677.
24. Stafford, G.; Kelley, P.; Syka, J. E. P.; Reynolds, W.; Todd, J. F. J. Int. J. Mass Spectrum. and Ion Proc. 1984, 60, 85.

What is claimed is:

1. A multi-stage particle separator for separating analyte from non-analyte solvent in a fluid sample which comprises
   nebulizing means for nebulizing the liquid sample to form droplets,
   means coupled to said nebulizing means for adding helium to the nebulizing means to nebulize the liquid sample,
   a desolvation chamber for receiving the droplets and terminating in a nozzle through which remaining droplets and newly formed particles flow, said particles increasing in velocity and exiting the nozzle at high velocity,
   a multi-stage momentum separator including skimmers positioned to receive said high velocity particles and allowing high velocity particles to pass therethrough,
   means for introducing a gas into one or more of said stages to increase the pressure of a latter stage to minimize the amount of solvent which flows to said stage from a preceding stage whereby particles leave said multi-stage momentum separator substantially free of solvent.

2. A multi-stage particle separator as in claim 1 in which said gas is applied only to the last stage.

3. A multi-stage particle separator as in claim 1 or 2 wherein said gas is supplied at a pressure which prevents contamination from associated vacuum pumping systems.

4. An ion trap mass spectrometer for mass analyzing a fluid sample including analyte and a non-analyte solvent comprising
   means for nebulizing the liquid sample to form droplets,
   a desolvation chamber for receiving the droplets and terminating in a nozzle through which remaining droplets and newly formed particles flow, said particles increasing in velocity and exiting the nozzle at high velocity, a multi-stage momentum separator including skimmers positioned to receive said high velocity particles and allowing high velocity particles to pass therethrough, means for introducing a gas into one or more of said stages to increase the pressure of a latter stage to minimize the amount of solvent which flows to said stage from a preceding stage whereby particles leave said multi-stage momentum separator substantially free of solvent in the form of a particle beam through a transfer line, an ion trap mass spectrometer coupled to said transfer line including a ring electrode and endcap electrodes, wherein at least one of said endcap electrodes is heated, defining an ion trap volume disposed to receive said particle beam such that said particle beam directly impinges one or more of said endcap electrodes for vaporization, means for ionizing said particles in said ion trap volume, means for applying voltages to said electrodes for trapping the ions, means for varying the voltages applied to said ion trap to eject ions from said trap and means for detecting said ejected ions and providing an indication of the mass of ejected ions to thereby provide an analysis of said analyte.

5. An ion trap mass spectrometer system as in claim 3 in which said gas is applied only to the last stage.

6. An ion trap mass spectrometer system as in claim 3 in which said trapping voltages includes an r.f. voltage whose amplitude is scanned to sequentially eject ions from said ion trap for detection and analysis.

* * * * *